United States Patent
Ritchie

(10) Patent No.: US 6,447,469 B1
(45) Date of Patent: Sep. 10, 2002

(54) ANKLE SUPPORT

(76) Inventor: Anthony L. Ritchie, 6313 S. Newland Ct., Littleton, CO (US) 80128

(*) Notice: Subject to any disclaimer, the term of this patent is extended or adjusted under 35 U.S.C. 154(b) by 0 days.

(21) Appl. No.: 09/477,840

(22) Filed: Jan. 5, 2000

Related U.S. Application Data

(60) Provisional application No. 60/114,817, filed on Jan. 6, 1999, now abandoned.

(51) Int. Cl.$^7$ ................................ A61F 5/00; A61F 5/37
(52) U.S. Cl. ............................. 602/27; 602/65; 128/882
(58) Field of Search ................................ 602/5, 27, 23, 602/65, 60–62; 128/882

(56) References Cited

U.S. PATENT DOCUMENTS

| | | | | | |
|---|---|---|---|---|---|
| 112,952 | A | * | 3/1871 | Niswander | 602/27 |
| 130,639 | A | * | 8/1872 | Howe | 602/27 |
| 487,492 | A | * | 12/1892 | Pugsley | 602/27 |
| 3,674,023 | A | * | 7/1972 | Mann | 602/65 |
| 5,038,762 | A | * | 8/1991 | Hess et al. | 128/80 H |
| 5,090,404 | A | | 2/1992 | Kallassy | |
| 5,099,860 | A | * | 3/1992 | Amrein | 128/882 |
| 5,199,941 | A | | 4/1993 | Makinen | |
| 5,298,013 | A | | 3/1994 | Lonardo | |
| 5,393,303 | A | * | 2/1995 | Shiono | 602/27 |
| 5,445,603 | A | * | 8/1995 | Wilkerson | 602/27 |
| 5,527,269 | A | | 6/1996 | Reithofer | |
| 5,620,413 | A | | 4/1997 | Olson | |
| 5,709,650 | A | | 1/1998 | Colman | |
| 5,741,222 | A | * | 4/1998 | Fiore | 602/27 |
| 6,056,713 | A | * | 5/2000 | Hayashi | 602/27 |

FOREIGN PATENT DOCUMENTS

| | | | | |
|---|---|---|---|---|
| DE | 38 38 582 | * | 1/1990 | 602/27 |
| GB | 2188550 A | * | 10/1987 | 602/27 |

* cited by examiner

*Primary Examiner*—Denise M. Pothier
(74) *Attorney, Agent, or Firm*—Ramon L. Pizarro; Edwin H. Crabtree

(57) ABSTRACT

An ankle support and method for providing ankle support over a user's foot. The ankle support includes a stiff stirrup and ankle strap having an elongated, generally straight shin portion and terminating in an elongated, generally straight stirrup portion, the stirrup portion being at an obtuse angle to the shin portion. Additionally, a flexible ankle strap attached to the stirrup and ankle strap and extending from the stirrup portion of the stirrup and ankle strap, away from the shin portion of the stirrup and ankle strap. A flexible shin strap attached the shin portion of the stirrup and ankle strap, so that the flexible ankle strap extends from underneath the wearer's foot, so that it is then wrapped around the ankle area and over the wearer's foot, while the shin strap is wrapped around the wearer's lower leg area behind the shin.

2 Claims, 3 Drawing Sheets ered embodiment of the invention about a person's foot.

ANKLE SUPPORT

REFERENCE TO RELATED APPLICATIONS

This application is a continuation of, and claims the benefit of, my provisional application having Ser. No. 60/114,817, filed Jan. 6, 1999, now abandoned.

BACKGROUND OF THE INVENTION (a) Field of the Invention

This invention generally relates to a wrapping and support system for the use over the ankle area of a person's foot. More particularly, and not by way of limitation, to an ankle support which includes a stiff inner body and an elastic outer wrap that is used to retain the inner body against the wearer's foot and leg.

(b) Discussion of Known Art

The prevention of injury to ankles, as well as the treatment of injured ankles, requires the provision of pressure and support to the area around the injured ankle. There are many known devices that for this purpose. However, the amount of support provided by these devices is often compromised by the need to provide the injured individual with mobility in order to prevent the accumulation of fluids around the injured area. Thus known devices have either provided excessive structure that inhibits the mobility of the user, which in turn has detrimental effects to the recovery of the individual, or provided too little support where needed.

Examples of known devices include U.S. Pat. No. 5,038,762 to Hess et al., U.S. Pat. No. 5,527,269 to Reithofer, and U.S. Pat. No. 5,090,404 to Kallassy.

SUMMARY

It has been discovered that the problems left unanswered by known art can be solved by providing an ankle support which includes:

- a stiff stirrup and ankle strap having an elongated, generally straight shin portion and terminating in an elongated, generally straight stirrup portion, the stirrup portion being at an obtuse angle to the shin portion;
- a flexible ankle strap attached to the stirrup and ankle strap and extending from the stirrup portion of the stirrup and ankle strap, away from the shin portion of the stirrup and ankle strap; and
- a flexible shin strap attached the shin portion of the stirrup and ankle strap, so that the flexible ankle strap extends from underneath the wearer's foot, so that it is then wrapped around the ankle area and over the wearer's foot, while the shin strap is wrapped around the wearer's lower leg area behind the shin.

It has been discovered that the disclosed arrangement will provide the user with support for the ankle area while providing the user with a significant amount of flexibility to continue use of the injured or weak leg.

Still further, it will be understood that the disclosed invention results in a support that is unobtrusive, so that the user may continue wear shoes and participate in sports or other activities as customary.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
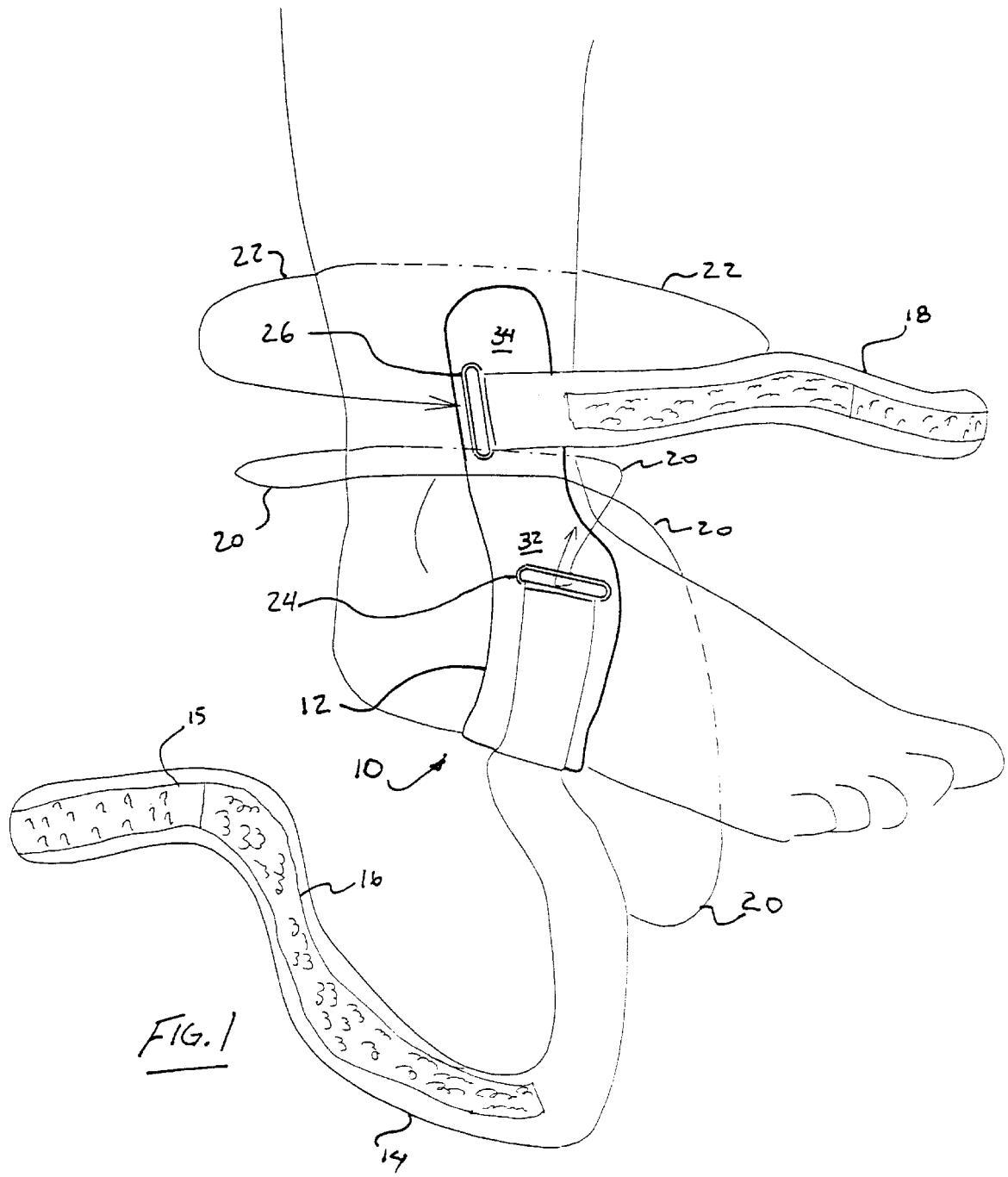
FIG. 1 is a perspective view of an embodiment of the invention illustrating the wrapping and mounting of a preferred embodiment of the invention about a person's foot.

Turning now to FIG. 1 where a preferred embodiment of an ankle support which has been referenced in the enclosed drawings as ankle support 10 for preventing injuries to and for supporting injured ankle joints. The support includes a semi-rigid or stiff section of material which can be bent to assume a generally L-shaped brace 12 which can then be mounted against the foot and against the leg. The brace is held against the leg and foot by means of a pair of straps. One strap, a stirrup or under-foot portion and ankle strap 14, extends from the brace, below the arch of the foot, up over the front of the foot just below the bottom of the tibia (neck of talus), around just above the exterior ankle, around the Achilles tendon (tendo calcaneus), around just above the interior ankle, down across the front of the bottom of the tibia, and attaches to a first adjustment loop 24 that is mounted on the mid portion of the brace 12.

The other strap of the invention, the lower calf strap 18, is designed to wind around the lower calf area (peroneus brevis) to lend support to the brace against the leg.

In the enclosed drawings FIG. 1 shows placement of the brace 12 against the foot. Arrow 20 indicates the direction of wrapping of the stirrup and ankle strap 14. Arrow 22 indicates the direction of wrapping of the lower calf strap 18. Adjustment of the stirrup and ankle strap 14 as well as the lower calf strap 18 is achieved through the use of hook 15 and loop 16 material mounted on the straps and rings 24 and 26 mounted on the stirrup and ankle strap 14 as well as the lower calf strap 18, respectively. The straps 14 and 18 are attached by means of an adhesive (or fasteners) against the brace 12.

Figure 2:
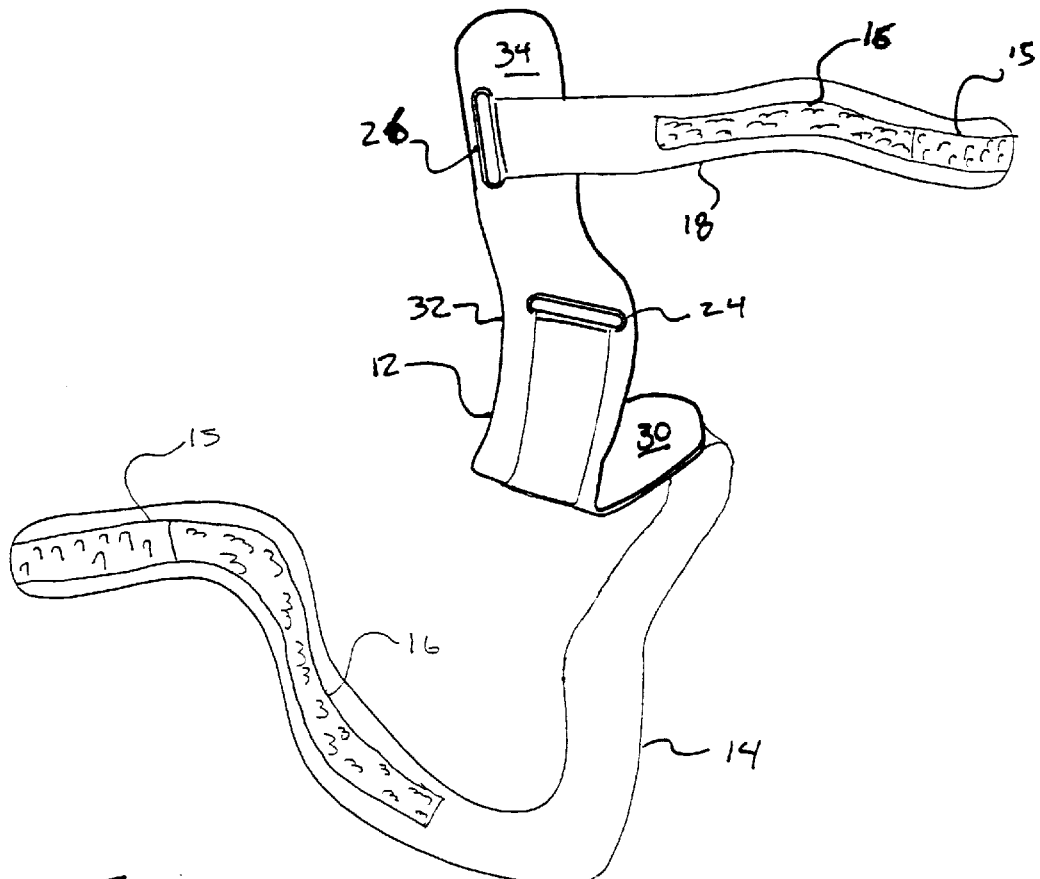
FIG. 2 is a perspective view of the invention.

FIG. 2 is a perspective view of the ankle support 10 alone.

Figure 3:
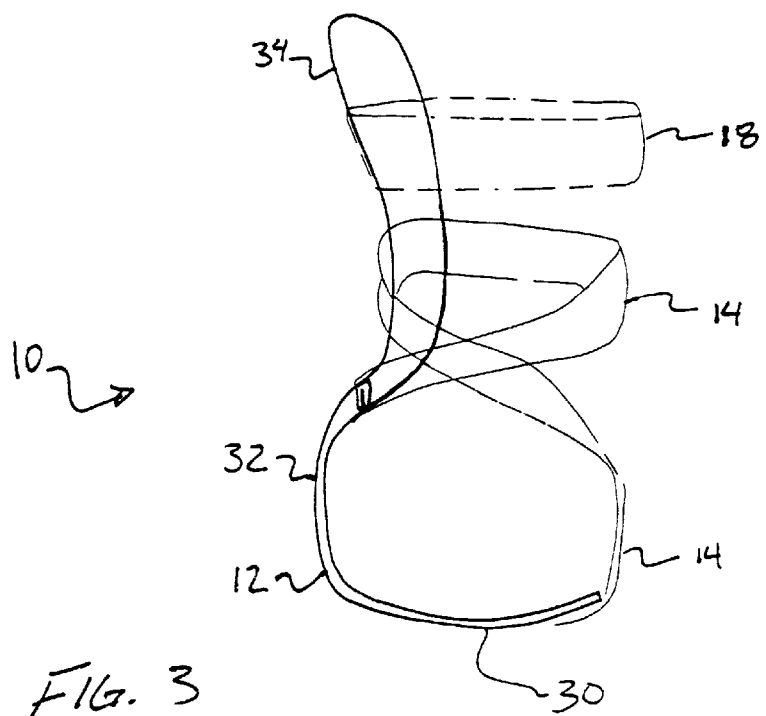
FIG. 3 is an end view of the invention, the view illustrating the preferred method of wrapping the straps about the wearer's foot. The wearer's foot was not illustrated for clarity.

FIG. 3 in a view of the ankle support 10 as if mounted on a person's right foot/leg, the view taken while looking at the front of the foot looking towards the back of the foot.

Figure 4:
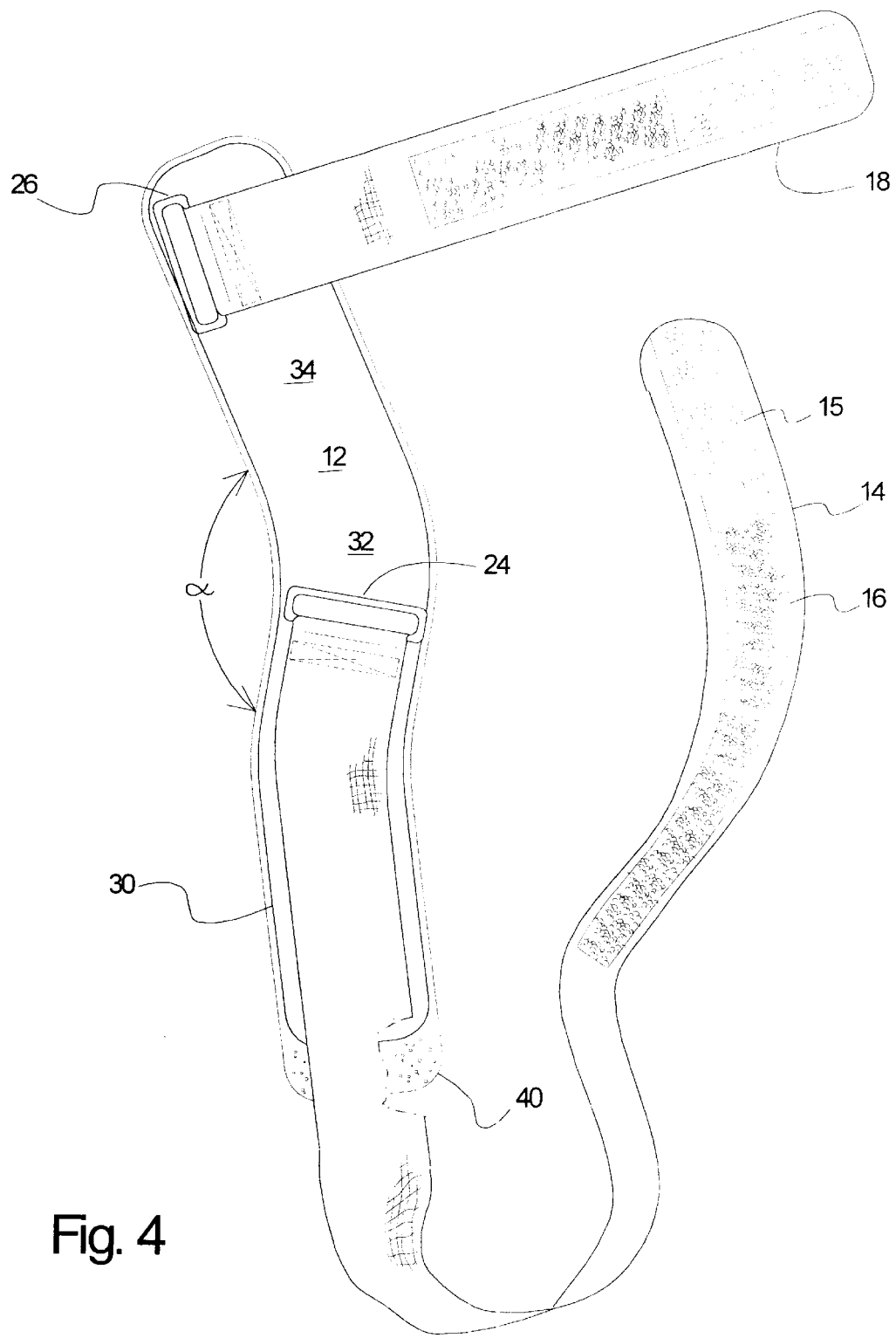
FIG. 4 is a view illustrating an embodiment of the invention. The embodiment shown in an extended, flattened form to illustrate the contour of a preferred embodiment of the invention.

FIG. 4 shows the brace 12 while spread out or flattened and the foam backing 40 that will preferably be used with the brace 12. The view shows that the brace 12 includes a stirrup portion 30, a mid portion 32 that is at an obtuse angle, x, to a shin portion 34. In use, the brace will assume an L-shape with the stirrup portion 30 assuming the position of the lower, horizontal, portion of the L, and the shin portion 34 together with the mid-portion 32 will assume the position of the vertical leg of the L. It is important to note that the mid-portion 32 will extend over the peroneus brevis, and to the external digitorum brevis. The shin portion will extend from the area of the mid-portion 32 that extends over the peroneus brevis and extend up over the external front portion of the leg, between the peroneus tertius and the peroneus brevis.

The described invention prevents injury to the ankle area by preventing rolling of the foot under tibia and thus causing damage or hyper extension of the anterior inferior tibiofibular ligament as well as the interosseous talo-calcanean ligament and other ligaments of the exterior portion of the foot by restraining any such movement by means of a cooperation of the stirrup and ankle strap 14 and the mid-portion 32 of the brace 12 against the tibia. The lower calf strap 18 supports the brace 12 against the lower part of the leg to ensure that load transferred to the brace 12 is reacted against the lower part of the leg or tibia.

It is important to note that while the disclosed invention has been described as being formable from a single sheet of material to form the stirrup and ankle strap 14, it is contemplated that a highly preferred embodiment of the invention will be made with a stirrup and ankle strap 14 that is made in a pre-shaped form by way of an injection mold. Clearly, it is also contemplated that additional stiffening materials, such as fiber reinforcements, such as graphite fiber or the like, may also be incorporated into the stirrup and ankle strap 14.

Thus it can be appreciated that the above described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. An ankle support for wearing over a person's foot, and providing lateral support by extending over a portion of a leg having a shin and a foot, the foot having an external portion opposite an arch, the ankle support comprising:

a stiff L-shaped stirrup and ankle brace of unitary construction, the stirrup and ankle brace having an elongated, generally straight shin portion and terminating in an elongated, generally straight stirrup portion, the shin portion being at an obtuse angle to a mid-portion and the stirrup portion defining the lower, generally horizontal portion of the L-shape, while the shin portion and the mid-portion define the vertical portion of the L-shape, the stirrup portion being of a length that has been adapted for extending over the external portion of the foot and under the foot, terminating near the arch area of the foot;

a flexible ankle strap attached to the stirrup and ankle brace, the flexible ankle strap including a first end and a second end, the first end of the flexible ankle strap being aligned with and extending away from a free end of the stirrup portion, the second end of the ankle strap being aligned and attached to the mid-portion of the ankle brace, the mid-portion of the ankle brace extending between the shin portion of the stirrup and ankle brace and the stirrup portion of the stirrup and ankle brace; and a flexible shin strap attached the shin portion of the stirrup and ankle brace, so that the shin portion of the stiff stirrup and ankle brace extends over a portion of the tibia while the stirrup portion of the stiff stirrup and ankle brace extends around the external part of the foot to approximately the arch area of the foot during use, allowing the flexible ankle strap to extend from underneath the foot to retain the stirrup portion of the stiff stirrup and ankle brace under the foot wrapped around the ankle area and over the foot, while the shin strap is wrapped around the leg area behind the shin during use.

2. A method for providing ankle support for wearing over a person's leg, the leg having a shin and foot the foot having an external portion opposite an arch, the method comprising:

providing support having:

a stiff, L-shaped stirrup and ankle brace of unitary construction, stirrup and ankle brace having an elongated, generally straight, flat shin portion and terminating in an elongated, generally straight, flat stirrup portion, the shin portion being at an obtuse angle to a mid-portion and the stirrup portion extending under the foot and terminating near the arch area of the foot when the shin portion is positioned over the shin of the leg;

a flexible ankle strap attached to the stirrup and ankle brace and extending from the stirrup portion of the stirrup and ankle brace, away from the shin portion of the stirrup and ankle brace; and a flexible shin strap attached the shin portion of the stirrup and ankle brace;

extending the flexible ankle strap from underneath the person's foot and over the foot and around the ankle area, so that it is then wrapped around the ankle area and over the person's foot; and wrapping the shin strap around the person's lower leg area behind the shin.

* * * * *